US012616454B2

(12) United States Patent
Chaffringeon

(10) Patent No.: US 12,616,454 B2
(45) Date of Patent: May 5, 2026

(54) SELF SAMPLING UNIVERSAL KIT, METHODS AND USE

(71) Applicant: V-VEIL-UP PHARMA LTD., Nicosia (CY)

(72) Inventor: Bernard Chaffringeon, Dubai (AE)

(73) Assignee: Bernard Marie Chaffringeon, Pitesti (RO)

( * ) Notice: Subject to any disclaimer, the term of this patent is extended or adjusted under 35 U.S.C. 154(b) by 323 days.

(21) Appl. No.: 15/733,140

(22) PCT Filed: Nov. 28, 2017

(86) PCT No.: PCT/IB2017/057456
§ 371 (c)(1),
(2) Date: May 28, 2020

(87) PCT Pub. No.: WO2019/106408
PCT Pub. Date: Jun. 6, 2019

(65) Prior Publication Data
US 2020/0390425 A1 Dec. 17, 2020

(51) Int. Cl.
*A61B 10/00* (2006.01)
*A61B 50/30* (2016.01)
*A61F 13/15* (2006.01)

(52) U.S. Cl.
CPC ...... *A61B 10/0045* (2013.01); *A61B 10/0038* (2013.01); *A61B 10/0096* (2013.01);
(Continued)

(58) Field of Classification Search
CPC ........ A61B 10/0045; A61B 2010/0074; A61B 10/0038; A61B 50/30; A61B 2050/3005;
(Continued)

(56) References Cited

U.S. PATENT DOCUMENTS 4,920,974 A 5/1990 Roth et al.
6,352,513 B1 * 3/2002 Anderson .......... A61B 10/0291
600/572
(Continued)

FOREIGN PATENT DOCUMENTS

JP WO8906360 A1 * 7/1989
WO 99/21521 A1 5/1999
(Continued)

OTHER PUBLICATIONS

English (Machine) Translation of WO8906360A1 (Year: 1989).*
(Continued)

*Primary Examiner* — Daniel L Cerioni
(74) *Attorney, Agent, or Firm* — Oliff PLC

(57) ABSTRACT
The present invention relates to a self-sampling kit and method for the universal sampling of at least one specimen such as a cell, cell residue, DMA, RNA, protein, virus, bacterium, parasite or fungus from the vaginal and/or rectal cavities of humans and animals, said kit comprising a self-sampling cloth (10) made of a flexible fabric with an absorbency of 3.5 g/g or less and a sealable recipient (50) for storing and transporting said sampling cloth (10). The present invention also relates to the use of the self-sampling cloth (10) for self-sampling of at least one specimen from bodily cavities of humans and animals, for instance for diagnosing an STI, such as an HPV infection.

17 Claims, 7 Drawing Sheets

(52) U.S. Cl.
CPC ........ *A61B 50/30* (2016.02); *A61F 13/15203* (2013.01); *A61B 2010/0074* (2013.01); *A61B 2050/3005* (2016.02); *A61B 2503/40* (2013.01); *A61F 2013/15471* (2013.01)

(58) Field of Classification Search
CPC ....... A61B 2503/40; A61F 2013/15471; A61F 13/15203
See application file for complete search history.

(56) References Cited

U.S. PATENT DOCUMENTS

| | | | |
|---|---|---|---|
| 6,475,165 B1 | 11/2002 | Fournier | |
| 2002/0032421 A1* | 3/2002 | Scott, Jr. | D04H 1/49 604/374 |
| 2003/0120180 A1 | 6/2003 | Kaylor et al. | |
| 2007/0129696 A1* | 6/2007 | Soerens | A61F 13/534 604/366 |
| 2009/0061151 A1* | 3/2009 | LaFond | B29C 66/961 156/73.4 |
| 2009/0098559 A1 | 4/2009 | Caragine et al. | |
| 2010/0286552 A1 | 11/2010 | Abitbol | |
| 2014/0073989 A1* | 3/2014 | Vom | A61B 90/06 600/572 |
| 2016/0324506 A1* | 11/2016 | Tariyal | A61B 5/157 |
| 2018/0125724 A1* | 5/2018 | Brown | A61F 13/2028 |
| 2018/0353737 A1* | 12/2018 | Chaffringeon | A61M 31/002 |
| 2019/0021703 A1* | 1/2019 | Dominguez-Bello | A61B 10/0045 |

FOREIGN PATENT DOCUMENTS

| | | |
|---|---|---|
| WO | 9921521 A | 5/1999 |
| WO | 2009/112527 A1 | 9/2009 |
| WO | 2013036447 A1 | 3/2013 |
| WO | 2017/115125 A1 | 7/2017 |

OTHER PUBLICATIONS

European Patent Office, International Search Report and Written Opinion Mailed Aug. 13, 2018 for PCT International Application No. PCT/IB2017/057456, International Filing Date Nov. 28, 2017.
European Patent Office (EPO), Office Action Mailed Aug. 25, 2022 for EP Application No. 17832090.9, regional phase of PCT International Application No. PCT/IB2017/057456, International Filing Date Nov. 28, 2017.

* cited by examiner

Fig. 1a                                        Fig. 1b

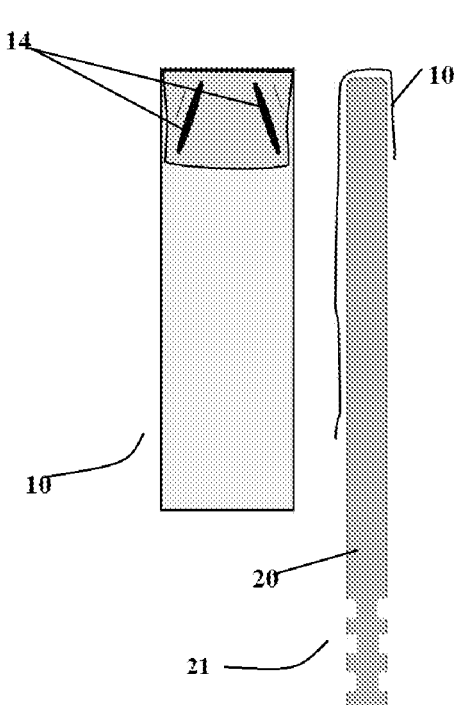
3a
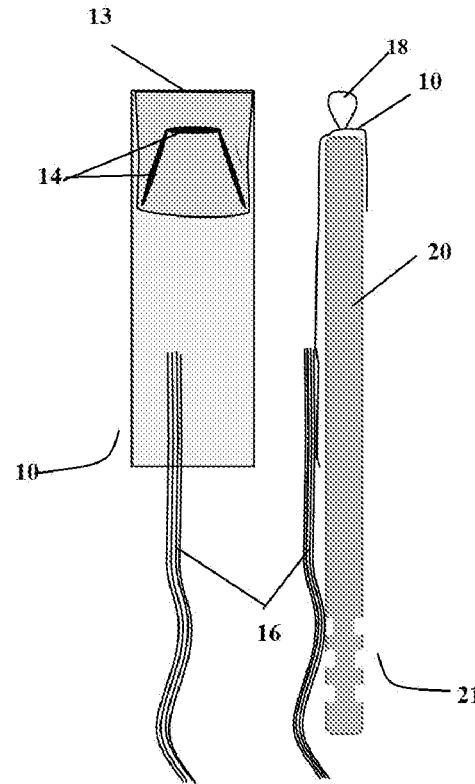
3b
Figure 3

5a

5b

5c

5d

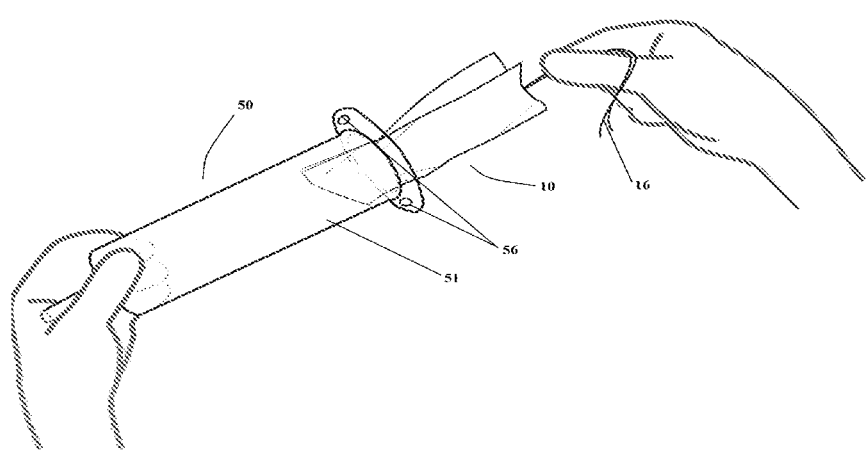
6a
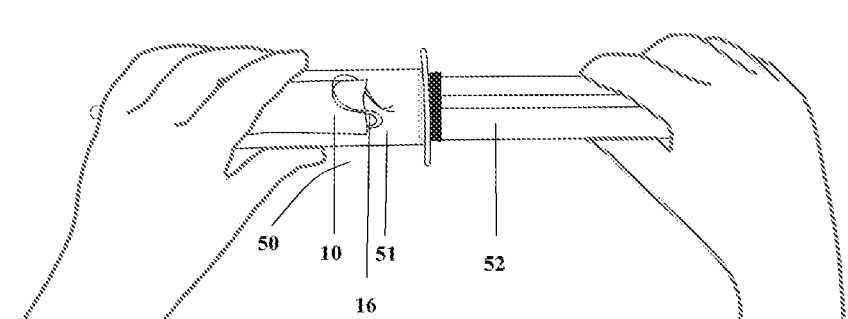
6b
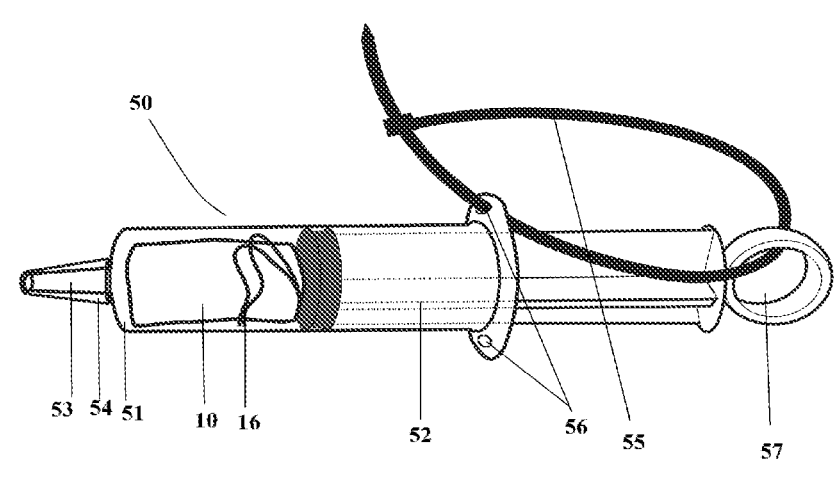
6c
Figure 6

| HPV | 6 | 11 | 16 | 18 | 26 | 31 | 33 | 35 | 39 | 40 | 42 | 43 | 44 | 45 | 51 | 52 | 53 | 54 | 56 | 58 | 59 | 61 | 66 | 68 | 69 | 70 | 73 | 82 |
|---|---|---|---|---|---|---|---|---|---|---|---|---|---|---|---|---|---|---|---|---|---|---|---|---|---|---|---|---|
| | | | c | c | c | c | c | c | c | | | | | c | c | c | c | | c | c | c | | c | c | c | | c | c |
| Vaccin G4 | x | x | x | x | | | | | | | | | | | | | | | | | | | | | | | | |
| Vaccin G9 | x | x | x | x | | x | x | | | | | | | | x | | x | | | x | | | | | | | | |
| #001 | | | | | | | | | | | | | | | | | | | | | | | | | | | | |
| #002 | | | | | | | | | | | | | | | | | | | | | | | | | | | | |
| #003 | | | | | | | | | | | | | | | | | | | | | | | | | | | | |
| #004 | | | | | | | | + | + | | + | + | | | | + | + | | | | | | + | | | | + | + |
| #005 | | | | | | | | + | | | | | | | | | | | | | | | | | | | | |
| #006 | | | | | | | | | | | | | | | | | | | | | | | | | | | | |
| #004v | | | | | | | | | | | | | | | | | | | | | | | | | | | | |
| #005v | | | | | | | | | | | | | | | | | | | | | | | | | | | | |
| #006v | | | | | | | | | | | | | | | | | | | | | | | | | | | | |

Figure 7

SELF SAMPLING UNIVERSAL KIT, METHODS AND USE

The present invention relates to the field of self-sampling for specimens such as cells, cell residues, proteins, DNA, RNA, and/or other material from bodily cavities such as the vaginal or rectal cavity.

BACKGROUND

According to the World Health Organization (WHO), more than 1 million sexually transmitted infections (STIs) are acquired every day worldwide. More than 30 different bacteria, viruses, fungi and parasites are known to be transmitted through sexual contact. Left untreated, they can lead to diseases, including cancer, damage of the reproductive organs and infertility. The most widespread STI, the Human papillomavirus (HPV) infection, causes more than 90% of cervical, vaginal, vulvar and anal cancer cases. 14 million new HPV infections occur every year according to the report of World Health Organization (2008). The incidence of such diseases can be significantly reduced by regular screenings. A regular Papanicolau cervical screening test (also known as Pap test, Pap smear or cervical smear) is recommended to identify pre-cancerous changes of the cells of the cervix, which can then be treated, preventing cervical cancer from developing. Also, a regular HPV testing is strongly recommended together with or separately from the Papanicolau test to determine the HPV strains. Prior to the Pap test and HPV screening, cervical cancer was the most common cancer in women. In countries where regular screening tests are available, mortality from cervical cancer has drastically reduced. Also, a regular screening for the other common STIs (such as *Trichomonas, Chlamydia, Gonorrhea, Candida, Neisseria, Mycoplasma*) will permit the timely treatment of such infections.

Collecting specimens such as cytological, DNA, RNA and/or biologic samples for testing, study and diagnosis of cervical cancer or STIs usually requires an examination and sampling made by a trained specialist (physician or nurse). Such samplings are traditionally performed on women by a gynecologist by inserting a speculum into the patient's vagina in a manner to expose the cervix of the uterus and then inserting a cervical scraper (with a swab or a brush) for sampling tissue from the endocervical canal and cervical os. The cervical scrapers are designed to scratch the tissue in order to take samples of tissue. Throughout this process, the woman must remain in a reclining (gynecological) position. Finally, the obtained specimen is applied directly on a glass slide, or placed into a recipient containing a liquid preservative in order to go through the analysis and evaluation steps. However, in about 30% of cases, unsatisfactory specimens are collected by this technique, leading to the need to repeat the procedure or to false or incomplete results.

Although regular screening (e.g annual) is highly recommended by health care standards-setting organizations, many patients do not screen regularly, especially in developing countries, due to different causes such as no or difficult access to a healthcare facility, or the fact that the procedure is painful, uncomfortable and embarrassing, time-consuming and expensive.

Some of these issues have been addressed by self-sampling devices, which are devices designed to be used by the patient without the presence and aid of a medical practitioner.

EP 2736419 discloses a device, a kit, and a method of use thereof, for self-administration and collection of cervical cell tissue samples such as for Pap smear testing. The device comprises an insertion tube, within which is carried a movable cervical aligning tool with an aligning probe, and a cellular sampling tool with a cellular adhesion surface. The aligning probe and cellular adhesion surface can be selectively movable relative to the insertion tube to improve accuracy of the testing and user safety. The method of collecting a vaginal and/or tissue sample consists of inserting the device into the vagina, advancing a ring from the inside of a tube for cervical cap alignment to enlarge the cervical fornix of the patient in order to expose the os, moving the sampling tool (provided with a cellular adhesion surface such as a small brush) outside the tube and then rotating the cellular sampling tool preferably two full rotations in each direction (clockwise and counter-clockwise), moving the elongated sampling tool back inside the tube to shield the sample within the insertion tube and withdrawing the device. Such a device is difficult to use by the patients and potentially painful. Moreover, the precision rate (accuracy) of such a self-test will be even more reduced than that of the classical Pap test sampled by the gynecologist, since the collecting is made in only one point (small area) inside the vagina, without any means to ensure that said point is actually the cervical os or an area under suspicion of having modified (cancerous) cells. Also, given the specific and complex structure of the device, it will have high productions costs, which will make it expensive and especially in developing countries.

U.S. Pat. No. 6,475,165 provides a cervical self-sampling device for self-sampling of culture material or specimens for use in thin smear technology techniques, microbiologic assay and epidemiologic studies, consisting of a 15 cm long tampon-like extendable tube preferably made of a medical grade cardboard material coated with wax or Teflon and housing an extrudable, retractable sponge. A handle is attached to the sponge to form a screw-cap lid, structured to be secured to a standard tube containing a fixative or preservative. Such a device is used by inserting the 15 cm long extendable tube in the vagina until resistance is met, then pushing the handle with the thumb while grasping the tube between the first two fingers to extend the sponge out of the tube, then rotating the handle to obtain the specimen, and then retracting to return the sponge inside the tube prior to removal. Like all other vaginal sampling devices, it is an important purpose of this device to be able to protect the sample from vaginal secretions. Such a device, though less painful than the previously mentioned one, remains relatively difficult to use. Also, the precision rate (accuracy) of such a self-test will be even more reduced than that of the classical test sampled by the gynecologist, since the collecting is made in only one point (small area) inside the vagina, without any means to ensure that said point is actually the cervical as or an area under suspicion of having modified (cancerous) cells or an infection. Moreover, the material of the sponge, which must be absorbent in order to work ("The vacuum created by the sponge upon insertion should draw cells down from the cervical canal") makes it difficult afterwards to extract the sampled cells from the material, thus decreasing the efficacy of the sampling (the final quantity of cells and DNA to be analyzed).

Hence, there remains a need for an inexpensive, painless and easy-to-use sampling kit that may be used without the assistance of a trained professional (such as a physician).

The aim of the present invention is to provide an inexpensive, painless and easy-to use self-sampling kit and method, with high precision rate and efficacy in sampling specimens like cells, cell residues, DNA, RNA, proteins and/or other materials of interests from the vaginal or rectal cavity This aim is achieved by a self-sampling kit according to the invention comprising a sampling cloth together with a suitable recipient. In another aspect, the present invention refers to the use of said sampling cloth for self-sampling at least one specimen from bodily cavities of humans and animals, in particular from the human vaginal or rectal cavity and to methods for self-sampling and diagnostic.

By self-sampling it is meant that the sampling procedure can be performed by an individual on him- or herself or by an individual on another individual, without the need of assistance from a trained professional. For animals, said self-sampling will be understood to be performed by a human.

By specimen it is meant any cell, cell residue, DNA, RNA, protein, virus, bacterium, parasite, fungus and/or other material of interests.

The self-sampling kit according to the invention comprises a sampling cloth designed to be inserted into the bodily cavity and a sealable recipient for storing and transporting said sampling cloth to a diagnosis facility such as a laboratory. The kit may further comprise an applicator for inserting the sampling cloth into the bodily cavity. The kit may further comprise instructions for use of the self-sampling kit and/or labeling means.

The method for self-sampling of the invention comprises the steps of (a) inserting a sampling cloth into the bodily cavity; (b) removing the sampling cloth from the bodily cavity; (c) placing the sampling cloth inside the recipient of the kit and (d) sealing the recipient.

The method for diagnostic of STIs (Sexually Transmitted Diseases) of the invention comprises the steps of: a) self-sampling at least one specimen from bodily cavities of humans and animals according to the self-sampling method of the invention described above; b) determining the presence of a STE by analyzing and identifying said at least one specimen from the sampling cloth.

As mentioned before, the sampling devices known in the art for sampling cells, nucleic acids or specimens for culture or microbiologic assays are designed to reproduce, as closely as possible, the traditional sampling process that takes place in the gynecologist's office. As such, they are concerned to protect the sampling tool from coming into contact with the bodily cavity walls and secretions (by keeping it inside a tube during insertion and extraction) and give advice on how to avoid the risk of contamination, i.e. of having the sampling tool touch any of the part of the vagina than the one targeted. They work on the assumption that cells and DNA from the uterus may be sampled only by collecting precisely from the cervical area, and they sample specimens from only a reduced area of the bodily cavity. Also, they work by a complicated methodology which must be correctly performed in order to obtain specimens of a quality comparable to those taken by a gynecologist. A key element of this methodology consists in attempting to contact the sampling tool (small brush or sponge) directly with the cervical os, manually move the sampling tool in a circular movement and then immediately retracting the sampling tool and extracting the device.

By contrast, the use of the sampling cloth according to the present invention is much simpler and less traumatic. The entire experience is physically and mentally comfortable, while at the same time rendering high quality results. The sampling cloth can be introduced into the bodily cavity easily, painlessly and in privacy. Said sampling cloth is easy to wear and may be comfortably left inside the bodily cavity for a period of time before it is extracted and housed in a separate recipient. Contrary to the above mentioned teachings of the prior art stating that the sampling must be made precisely in the cervical area, we have found that the use of the sampling cloth succeeds every time in collecting cells and nucleic acids from the uterus. Actually, the specimens collected by using the sampling cloth of the invention contain significantly more material of interest such as cells, DNA, proteins, resulting in a more complete and accurate detection, than specimens taken by a doctor or a nurse in the traditional manner. These surprising findings have been proven by rigorous assays, the results of which will be presented in more detail later in this description. These assays show that, by using the sampling cloth of the invention, up to 10 times more HPV DNA has been collected from each individual than by using the traditional sampling process. Also, more strains of HPV have been diagnosed for each tested subject from the samples collected with the self-sampling kit and method of the invention, resulting in a more correct and complete diagnosis of the HPV infections than from samples collected by a trained professional using the traditional sampling method in a medical facility. Additionally, by getting into contact with virtually the entire surface of the bodily cavity, as well as the external tissues, every potential specimen of interest (such as cells, nucleic acids, proteins, viruses, bacteria, parasites or fungi) may be caught by said sampling cloth and released when needed.

The sampling cloth of the invention may also be used for:
collecting samples for detecting bacteria (such as *Neisseria gonorrhea, Chlamydia trachomatix, Mycolpasma hominis, Mycoplasma urealyticum, Syphilis, Streptococcus*), parasites (such as *Trichomonas vaginalis*) or fungi (such as *Candida albicans*).
testing for hemoglobin resulting from the premature rupture of membranes (PROM) during pregnancy. PROM represents the breakage of the amniotic sac before the onset of labor. If rupture occurs before 37 weeks, it is called preterm premature rupture of membranes (PPROM), and the fetus and mother are at greater risk for complications. Premature rupture of the membranes provides a path for bacteria to enter the womb and puts both the mother and fetus at risk for life-threatening infection. Low levels of fluid around the fetus also increase the risk of umbilical cord compression and can interfere with lung and body formation in early pregnancy. The presence of hemoglobin in the vagina signals the onset of PROM. Very small quantities of hemoglobin are present in the vagina starting 24 hours before the onset of the PROM. The timely detection of such very small quantities of hemoglobin would allow the pregnant woman to seek medical help and to eventually prevent the rupture or contain the effects. Using the self-sampling kit of the invention, pregnant women at risk of premature rupture of membranes (PPROM) will be able to frequently self-sample and test for the presence of hemoglobin, without having to travel to the medical facility or to stay into the hospital.
in case of sexual aggression, the sampling cloth may be used to collect the aggressor's DNA.

The sampling cloth according to the invention is designed to be inserted into the vaginal or rectal cavity of a human or animal, by means of an applicator. Thus, a direction of insertion is defined, which is an axis crossing the sampling cloth and being oriented from the end of the sampling cloth that last contacts the cavity or remains outside the cavity, called distal end of the sampling cloth, to the end of the sampling cloth that first contacts said cavity, called proximal end of the sampling cloth. When looking in the direction of insertion, the top of the sampling cloth or the upper part is represented by the extremity of the sampling cloth that comprises its proximal point; that is the point that first contacts the cavity. At the same time, the bottom of the sampling cloth or the lower part is represented by the extremity of the sampling cloth that comprises its distal end; that is the point of the sampling cloth opposite to the proximal point, i.e. placed at the furthest distance from the proximal point on the insertion direction. In some embodiments, part of the sampling cloth may protrude outside from the vaginal or rectal cavity. In such a situation, the bottom of the sampling cloth will also comprise such part of the sampling cloth. Taking into account the above definitions, then lateral sides of the sampling cloth will be the left and right extremities, considering the top and bottom as defined above.

The upper edge of the sampling cloth is the edge on the top of the sampling cloth while the lower edge of the sampling cloth is the edge situated on the bottom of the sampling cloth. According to the invention, "upper", "up" or "above" will refer to a first point or part situated closer to the top of the sampling cloth relative to a second point of reference, while the second point will be situated "lower", "down" or "below", respectively, to said first point or part.

According to the invention, "oriented upwards" means oriented towards the top of the sampling cloth while "oriented downwards" means oriented towards the bottom of the sampling cloth. By "moving forward" it is to be understood according the invention movement in the direction of insertion of the sampling cloth into said cavity.

One aspect of the present invention refers to a self-sampling kit comprising a sampling cloth and a sealable recipient for storing and transporting said sampling cloth.

A further aspect of this invention refers to the use of a sampling cloth for self sampling of at least one specimen from bodily cavities of humans and animals.

The mentioned sampling cloth of the invention is made of a material suitable to be introduced into the vagina or rectum, Thus, the sampling cloth can be comfortably fitted inside the bodily cavity.

Said suitable material will be flexible, by which it is to be understood a material hat will bend and unbend to follow the shape of the vagina or rectum. Also, a suitable material will be preferably atraumatic, by which it is to be understood a material that may be put into contact with or made to slide over or wipe a surface of a body membrane such as the vaginal or rectal mucosa without causing any injury or discomfort such as irritation, pain etc., preferably a fabric with a soft carded smooth surface. The use of a sampling cloth made of such a flexible, atraumatic material has the advantage that avoids the irritation of the vaginal cavity, pain and discomfort during the insertion that are usually associated with the use of the devices from the state of the art. Preferably, when the sampling cloth is introduced into the vagina with the aid of an applicator, the sampling cloth above and around said applicator will protect the vaginal mucosa from direct contact with the hard material of the applicator.

Advantageously, a suitable material for the sampling cloth is a material that can catch specimens from the bodily cavity and preferably retain said specimens on its surface, while at the same time being able to subsequently easily release said specimens so that they can be analyzed. Therefore, the sampling cloth has advantageously a surface coming into contact with the bodily cavity, but little or no absorbency, so that only a small amount of the specimens are absorbed into the fabric of the sampling cloth. According to the invention, the absorbency should be less than 3.5 g/g, preferably less than 3 g/g, more preferably less than 2 g/g measured using the Syngina protocol for measuring the absorbency of tampons. For example, an absorbency of 3.5 g/g means that 3.5 grams of liquid are absorbed per 1 gram of material. Preferably, the sampling cloth is made of a fabric having low thickness. A sampling cloth having low thickness will be able to catch the specimens on its surface, but it will not, or only minimally, transfer, collect and retain them in its depth. Such a sampling cloth has the advantage that, unlike a sponge or a tampon, it will not retain inside the collected specimens (cells, proteins, DNA, etc.) during the analysis and evaluation steps. Instead, the sampling cloth will easily liberate the specimens from the sampling cloth, so the final quantity of specimens to be analyzed is maximized, which raises the precision rate (accuracy) of the sampling test. The thickness of the sampling cloth should be of 3 mm or less, preferably 2 mm or less, more preferably 1 mm or less, even more preferably 0.6 mm or less, which means a thickness much smaller compared to a normal tampon. Advantageously, the material of the sampling cloth has a basis-weight of approximately 60 g/m$^2$.

The material of the sampling cloth, suitable to be comfortably inserted into a bodily cavity, may be chosen from the group of a woven or non-woven textile, for example made of synthetic fibers (such as polyester, polypropylene, polyethylene, polyamide, polyacetate, polyvinyl acetate), semi-synthetic fibers (such as viscose, modal, lyocell), plant fibers (such as cotton), animal fibers (such as silk), or combinations thereof. In a preferred embodiment, the material is biodegradable, thus reducing the impact on the environment. Preferably, the material is a non-woven textile made of synthetic fibers, since such materials are atraumatic and have the desired low absorbency. Also, such products may have low production costs. In a preferred embodiment, the material is also thereto-fusible, so that it may be welded. In a more preferred embodiment, the sampling cloth is made of a non woven fabric with a soft carded smooth surface comprising a non-woven polyethylene/polyester bicomponent. Preferably, such material has the following properties:

- average basis weight (mass per unit area), measured with WSP 130.1 Test method, of around 59.20 g/m$^2$,
- average tensile strength MD, representing the force per unit width which is required to rupture a sample orientated in the machine direction, measured with a Test method following WSP 110.4 using a sample width of 25.4 mm (1 inch), a clamp distance of 127 mm (5 inch) and a speed of 500 mm/min (19.7 inch/min), of around 48.86 N/inch
- average elongation at F-max MD, representing the relative increase in length at the maximum force applied on a sample orientated in the machine direction, measured with a Test method following WSP 110.4 using a sample width of 25.4 mm (1 inch), a clamp distance of 127 mm (5 inch) and a speed of 500 mm/min (19.7 inch/min), of around 38.40%.

In a preferred embodiment, the sampling cloth according to the invention may have a region having a rougher surface than the rest of the sampling cloth (such as more roughly checkered organic cotton, linen or burlap), preferably placed so that it is most likely to reach and, by scratching the tissue, collect samples from a targeted area of the bodily cavity. For example, in order to collect samples from the cervical os, the rougher fabric can be placed at the top of the sampling cloth. The rougher fabric may, for example, be attached to the fabric of the sample cloth by any suitable means such as gluing, welding, sewing, etc, or it may be integral part of the sampling cloth. A sampling cloth having such a region with a rougher surface will be able to collect, in less time, specimens from the targeted area.

The sampling cloth according to the invention is suitable to be inserted into the vaginal or rectal cavity of a human or animal. Thus, the person skilled in the art will understand to choose the dimensions of the sampling cloth adapted to the dimensions of the bodily cavity where it is to be inserted.

The vagina and rectum are open cavities in the form of fibro-muscular tubes with walls that are easily distensible. The vagina is in the form of a tube having at the extremities an external opening (the vaginal opening) and an internal opening (communicating with the uterus). The rectum is in the form of a tube having at the extremities an external opening (the anus) and an internal opening (communicating with the large intestine); near the external opening it has a dilated portion, the rectal ampulla, where the sampling cloth according to the invention is meant to be housed. The external openings of the vagina and rectum are substantially circular. The width (diameter) of the tubes (vagina and rectum) varies throughout their length, with the minimum width being at the external opening of the bodily cavity. For example, the human adult vagina or rectum at rest have, at the external opening, a width of about 2.5 cm.

Whatever the shape of the sampling cloth when outside the bodily cavity, due to the fact that it is made of a flexible fabric, when inserted into the bodily cavity by pushing it through the substantially circular external opening, the sampling cloth will collapse, e.g. deform, fold, strangle and/or twist to pass through the external opening and then will unfold to roughly follow the shape of the cavity. Therefore, the dimensions of the sampling cloth for inserting into the human vaginal or rectal cavities will be chosen such that, in said collapsed position, the maximum width of the sampling cloth will be of less than 2.5 cm, so that it can be comfortably inserted into the bodily cavity. In a preferred embodiment, when using a sampling cloth of a substantially rectangular shape, the width of said rectangle may be chosen, for example, to be between 2 cm and 6 cm.

When inserted into the bodily cavity, which means after the sampling cloth has been pushed inside the bodily cavity, the sampling cloth will preferably take a shape having the proximal end closest to the internal opening of the bodily cavity and the distal end closest to the external opening of the bodily cavity, and will occupy a roughly tubular space. The distance from the proximal end to the distal end of the sampling cloth defines the length of the sampling cloth. Thus, the skilled person will be able to shape/choose the dimensions of the sampling cloth so that when inserted into the bodily cavity, the sampling cloth will preferably have a length up to the maximum length of the vagina or of the rectal ampulla. In a preferred embodiment, the length of the sampling cloth after insertion into the bodily cavity is equal or slightly less than the length of said bodily cavity, so that specimens from virtually all the surface of the cavity may be sampled. In another embodiment, the sampling cloth may have a length greater than the maximum length of the bodily cavity, so that part of the sampling cloth protrudes outside of the bodily cavity, in order to collect specimens from the area outside the cavity (such as vulva or anal orifice). Preferably, the part of the sampling cloth that protrudes outside may be used as means of removal for the extraction of the sampling cloth from the bodily cavity, and also for sampling specimens from the outside area or even from the other bodily cavity.

For example, the length of the human adult vagina at rest varies from about 5 to about 14 cm, and the length of the human adult rectal ampulla varies from about 4 to about 6 cm. The skilled person will preferably choose the dimensions of the sampling cloth for completely inserting into the vagina of a human so that, when inserted, the sampling cloth will have the length approximately equal or slightly less than the human vagina so that it can collect specimens from all parts of the vagina. Therefore, the skilled person will choose in this case a sampling cloth with a length of less than 14 cm, such as about 12 cm, about 10 cm, about 8 cm or less, preferably of about 10 cm.

For insertion in the human rectum the sampling cloth will be smaller, in order to stay in the rectal ampulla, for example having a length of less than 5 cm, preferably less than 3.5 cm.

In another preferred embodiment, the length of the sampling cloth is chosen to be longer than the human vagina (i.e. longer than 12 cm, preferably of about 14 cm, about 16 cm, about 18 cm, about 20 cm, about 22 cm or longer), so that it will protrude outside of the human vagina during use. A sampling cloth that protrudes outside the human vagina would have the advantage that it would be able to collect specimens from the end of the vaginal cavity, on the vulva, around the anal orifice, and also, if necessary, it may be introduced inside the anus so that it collects also from that area. This way the sampling cloth will catch specimens from infections located outside the vagina (such as, for example, genital warts). Also, a sampling cloth that protrudes outside the vagina has the advantage that it may be withdrawn from the vagina by pulling on the segment left outside; therefore the sampling cloth will not need any means for removal, making it simpler to produce, less expensive, and less harmful, as there is no need to attach means for removal to the cloth, thus no hard spot is created.

The sampling cloth can be made of at least one sheet of fabric having any suitable shape; preferably it may have, for example, a substantially rectangular, square, trapezoidal, parallelepipedic, oval or circular shape. Alternatively, the sampling cloth may comprise one or more fringes or strings, such as strips or cords.

In another preferred embodiment, the sampling cloth is shaped from a sheet of fabric having a folded area at the proximal end by folding the sheet over a folding line. Said folded area is provided with guiding elements for guiding and maintaining the applicator within the folded area during insertion, and also for maintaining the folded area in position. For example said guiding elements may be in the form of welding lines, along which the fabric of the two sides of the fold are welded together. Said guiding elements define a pocket area of the folded area, wherein the applicator is placed during the insertion of the sampling cloth within the bodily cavity. Said guiding elements will be placed so that the applicator is guided towards the folding line and maintained in a substantially fixed position within the pocket area during the insertion of the sampling cloth in the bodily cavity, and so that after insertion, the applicator will be easily released from the pocket area and removed from said cavity by moving the applicator in the opposite direction to the one of insertion, without removing also the sampling cloth. To this end, the guiding elements are placed so that the maximum distance between them is about 2-6 mm bigger than the biggest section, such as the diameter, of the head (proximal end) of the applicator, for a smooth insertion and removal of the applicator. In a preferred embodiment, the sampling cloth having a folded area has a substantially rectangular shape, with the proximal end being folded once and provided with welded guiding elements. In another preferred embodiment, the shape of said sampling cloth before folding the proximal end is substantially a parallelogram or an isosceles trapezoid, so that one substantially triangular extremity can be folded to form the folded area, while the other substantially triangular area forms the distal extremity of the sampling cloth, which is placed at the narrower zone of the bodily cavity or outside it. Such a shape has the advantage that less raw material is used for producing a sampling cloth having about the same catching surface.

In another embodiment, the sampling cloth of the invention comprises one or more fringes, such as strips, cords or strings. Advantageously, when the sampling cloth is made of one string, said string may have a thickness of more than 3 mm, preferably of 10 mm or less, as long as the capacity to catch and release specimens is not impaired in a preferred embodiment, the sampling doth comprises a multitude of fringes, such as strips and/or cords in another preferred embodiment, the sampling cloth may be made of at least one strip or cord, which is folded to form a multitude of fringes. Such a sampling cloth will advantageously maximize the contact surface between the sampling cloth and the targeted tissues and allow the sampling cloth to reach different areas of the bodily cavity. Said strips or cords may optionally have various lengths, preferably they have gradually increasing lengths. More preferably, at least one of the strips and/or cords has a length sufficient to protrude outside the bodily cavity, thus being able to collect specimens from the outside area and optionally from the other bodily cavity and can also serve as means of removal. Said fringes are provided with means to hold them together, such as a point of welding, gluing, a knot or a joining element. For example, such a joining element may be made from the same material as the sampling cloth or from another material such as plastic.

The sampling cloth according to the invention may be provided with means of removal, for removing the sampling cloth from the cavity after use. The means of removal may be, for example, at least one thread, string, strip, ribbon, wire etc., with a length adapted for the extraction of the sampling cloth from the bodily cavity or longer (suitable to reach to and collect specimens from the other bodily cavity). It may be made of any material which does not tear when a force necessary to extract the sampling cloth from the bodily cavity is applied thereon. Preferably, rupture resistance of such means is above 50 N. A preferred means of removal is a cotton yarn having a metric yarns number Nm of 16/4.

Advantageously, the means of removal will also be able to catch specimens from outside the bodily cavity. For instance, the means of removal of a vaginal cloth will catch the specimens from the end of the vaginal cavity, on the vulva, around the anal orifice, and also, if necessary, may be introduced inside the anus so that it collects also from that area. Since the entire sampling cloth, including the removal means, is housed into the recipient of the kit and is then subjected to the same treatments for releasing the specimens therefrom, the surface of the means of removal will advantageously be able to catch and release samples from different areas. For this reason, said removal means will advantageously not undergo the treatments known in the art for rendering them hydrophobic (such as treating them with water repellent substances, for example covering them with a water repellent wax). As such, the removal means of the invention will be safer to use and also able to sample specimens.

The means of removal may be attached to the sampling cloth in any suitable way known in the art that would allow a good fixation, without detaching from the sampling cloth during use or removal, such as by welding, sewing, pasting, stapling, buttoning, knotting or gluing.

In a preferred embodiment, the means of removal may be attached in one or more points situated on an axis of symmetry of the sampling cloth substantially parallel to the direction of insertion into the vagina or rectum or forming with said direction of insertion an angle of no more than 45°.

The sampling cloth according to the invention may be inserted into the bodily cavity by using an applicator which may be a finger, or a pushing tool. The pushing tool or applicator will have a shape, and dimensions adapted to those of the bodily cavity for which it is intended and the strength necessary to be able to push the sampling cloth inside the bodily cavity. The applicator may be disposable (one use-only) or reusable. The applicator may be made of any suitable material, such as plastic, silicon, wood, metal (such as stainless steel, titanium, or gold plated), cardboard etc. Preferably, the applicator is made of low density polyethylene PE-LD, which has low production costs, good flexibility, low weight and can be cleaned and reused.

The applicator may be releasably inserted, centered or off centre, in a dedicated pocket of the sampling cloth. Preferably, the width of said pocket is 2-6 mm bigger than the diameter of the applicator, for a smooth insertion and removal. Optionally, the applicator may have a gripping area, for gripping during insertion of the sampling cloth and during removal of the applicator from the bodily cavity. Said gripping area may have an adherent surface, or may be shaped so that it can be easily and firmly held by the human hand. For example, the applicator may have, along the gripping area, a series of recesses or elevations.

For instance, the pushing tool may be made in the form of a tubular body, having a proximal end (head), which is the end that first enters the bodily cavity and a distal end, which is the end remaining outside the bodily cavity and being optionally provided with gripping means. For human use, such an applicator may have a length (the height of the tube) of about 120 mm and a width (diameter of the tube) of about 11 mm.

In another preferred embodiment, for a sampling cloth in the form of a multitude of fringes, the applicator is advantageously in the form of a tubular body having a proximal end provided with a depression for housing the fringes of the sampling cloth during insertion, or, alternatively, for receiving the joining element of the sampling cloth during insertion.

The self-sampling kit of the invention comprises a sampling cloth as described above, together with a suitable sealable recipient for storing and transporting said sampling cloth to a diagnosis facility. The kit may further comprise an applicator as described above for inserting the sampling cloth into the bodily cavity. The kit may further comprise instructions for use of the self-sampling kit and/or labeling means for attaching a label to the recipient.

The recipient of the self-sampling kit is made of a suitable standard material such as plastic, and has the dimensions adapted to house the entire sampling cloth. Said recipient is provided with at least one opening equipped with sealing means. At least one of the openings of said recipient has dimensions sufficient to allow the user of the kit to easily place the sampling cloth inside the recipient, preferably without squeezing the cloth, which might result in removing part of the collected specimens. Therefore, the dimensions of said opening will depend on the width of the sampling cloth. For example, said recipient may be in the form of a plastic jar or tube provided with a thread cap. Optionally, said recipient may contain means for preserving the specimen or further preparing it for a desired subsequent examination, such as saline water, culture medium (for bacterial analysis), KOH solution (for fungal analysis), etc.

In a preferred embodiment, the recipient is a syringe, comprising a barrel, piston and a discharge orifice provided with sealing means such as a cap. A recipient shaped like a syringe has the advantage that, upon arrival at the examining facility (laboratory), it may be used to draw a convenient substance (such as a saline solution) directly into the recipient. Also, the piston may be repeatedly moved in and out of the barrel to agitate the contents and free the specimens from the sampling cloth. Also, when discharging the specimen, the piston may be pushed as far as possible, thereby thoroughly whipping the walls of the barrel and squeezing the sampling cloth, so that the largest possible quantity of specimens will get discharged from the barrel through the discharge orifice. In consequence, no further devices and manipulation are needed to discharge the specimens from the recipient, and very little specimens are lost, resulting in a very effective process and high quantity of examined specimens. After introducing the sampling cloth into the recipient, the piston of the syringe-like recipient will be used to seal the opening of the barrel. Preferably, the recipient will be further provided with stopping elements for fixing and sealing the piston into place inside the barrel. For example, such stopping elements may consist of adjustable plastic strips adapted to pass through orifices provided in the piston and barrel, thus sealing together the piston and barrel in the desired position. Such stopping elements ensure that the recipient remains sealed until it reaches the laboratory and that any tampering with or violation of the recipient will be evident.

Optionally, the recipient may be provided with labeling means, such as a label for writing the data of the patient from whom the sample was taken.

The method for self-sampling of the invention comprises the steps of (a) inserting a sampling cloth into the bodily cavity; (b) removing the sampling cloth from the bodily cavity; and optionally (c) placing the sampling cloth inside a sealable recipient and (d) sealing the recipient. Thus, the sampling cloth may be directly tested or placed in a sealed recipient, which may be then taken or sent to a testing facility, such as a laboratory, for analysis and diagnostic.

Depending on the specific circumstances (such as the humidity inside the user's bodily cavity, the targeted specimen, the type of sampling cloth used, etc.), the sampling cloth of the invention may be left inserted into the bodily cavity for a period of time. The sampling cloth of the invention is advantageously very comfortable to wear inside a bodily cavity.

In a preferred embodiment, for collecting HPV DNA from the human vagina, the sampling cloth of the invention may be maintained inserted into the vagina for at least 2 minutes, preferably for 30 minutes, 1 hour, 2 hours, 3 hours or more.

Our tests have shown that, by using the method of self-sampling of the invention, significantly more specimens are sampled than by using the traditional sampling methods (sampling by a trained professional such as a physician or a nurse) or by using the self-sampling devices known in the field.

The method for diagnostic of STIs (Sexually Transmitted Diseases) of the invention comprises the steps of: a) self-sampling at least one specimen from bodily cavities of humans and animals according to the self-sampling method of the invention described above; b) determining the presence of a STI by analyzing and identifying said at least one specimen from the sampling cloth.

As mentioned before, by using the method of self-sampling of the invention, more specimens are sampled than by using other methods, therefore the diagnostic method of the invention will be more accurate.

BRIEF DESCRIPTION OF THE DRAWINGS

FIG. 3 represents a front view of different embodiments according to the invention wherein the sampling cloth is in the form of a single-sheet fabric having a folded area and guiding elements, together with applicators.

FIG. 6 represents views of the steps according to an embodiment of the invention for placing the sampling cloth within a syringe-shaped recipient, closing and securing said recipient.

FIG. 7 represents a table showing trial results obtained by using the sampling cloth of the invention for detection of HPV strains as compared with conventional methods of sampling by a trained professional.

FIGS. 1a and 1b depict two embodiments of a sampling cloth (10) according to the invention wherein the sampling cloth (10) is in the form of rectangular fabric consisting of a sheet (1) of fabric and is provided with a pushing area (11) which has with an orifice (12), preferably in a central position with respect to the pushing area. As shown in FIGS. 1a and 1b, said pushing area may be placed at different positions along the length of the sampling cloth (10), preferably closer to the proximal end of the sampling cloth (10). In a preferred embodiment, the sampling cloth (10) in the form of a rectangle has a length of about 18 to 22 cm; and a width of about 3 to 6 cm.

Figure 1:
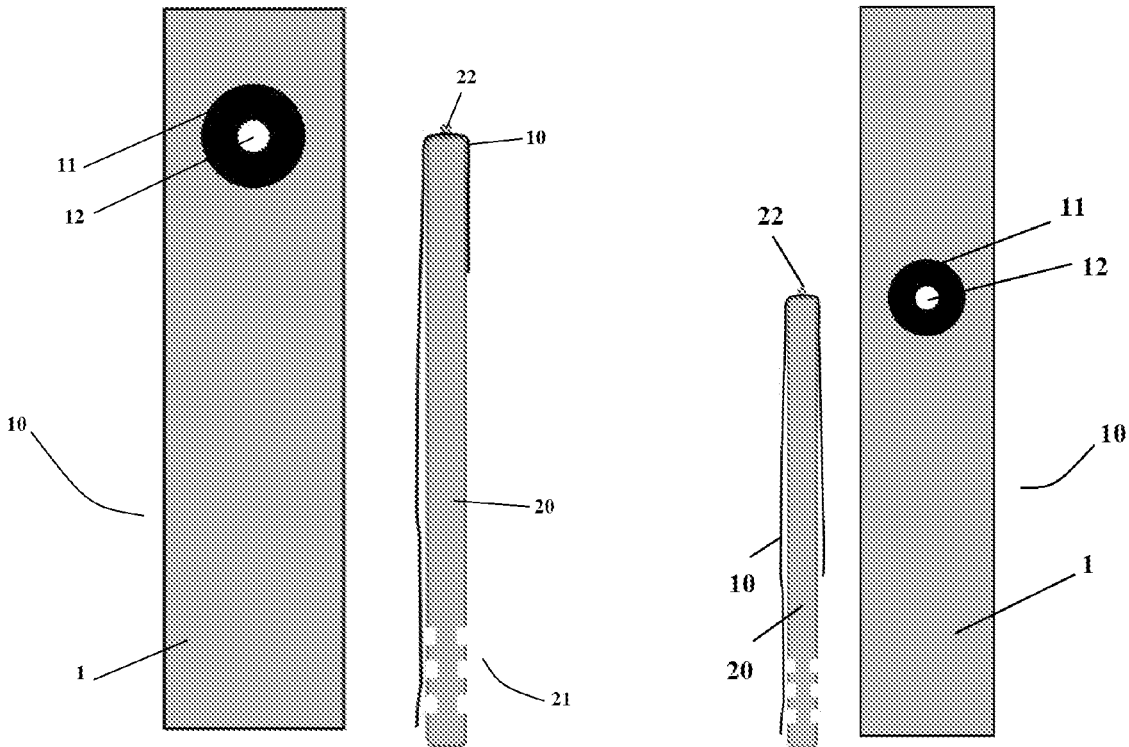
FIG. 1 represents a front view of preferred embodiments according to the invention wherein the sampling cloth is in the form of a single-sheet

An applicator (20) for the insertion of the sampling cloth (10) inside the bodily cavity is also depicted, and the position of the sampling cloth (10) on the applicator (20) before insertion into the bodily cavity. Said applicator (20) is substantially in the form of a rod, and has a proximal end which is the end that will be inserted into the bodily cavity, and a distal end, which is the end that remains outside the bodily cavity. The proximal end of the applicator (20) is provided with a protuberance (22). The protuberance (22) has a diameter less that the diameter of the orifice (12), such that it can reversibly protrude through the orifice (12), while the proximal end of the applicator has a diameter larger that the diameter of the orifice (12), so that it cannot protrude through the orifice (12). Therefore, the proximal end of the applicator (20) will be able to push the sampling cloth (10) within the bodily cavity, while the protuberance (22) passing through the orifice (12) will keep the applicator (20) connected with the sampling cloth (10). The distal end of the applicator (20) is provided with a gripping area (21) consisting, in this example, in a series of recesses in the material of the applicator. In a preferred embodiment, the length of the applicator (20) is of about 12 cm.

Figure 2:
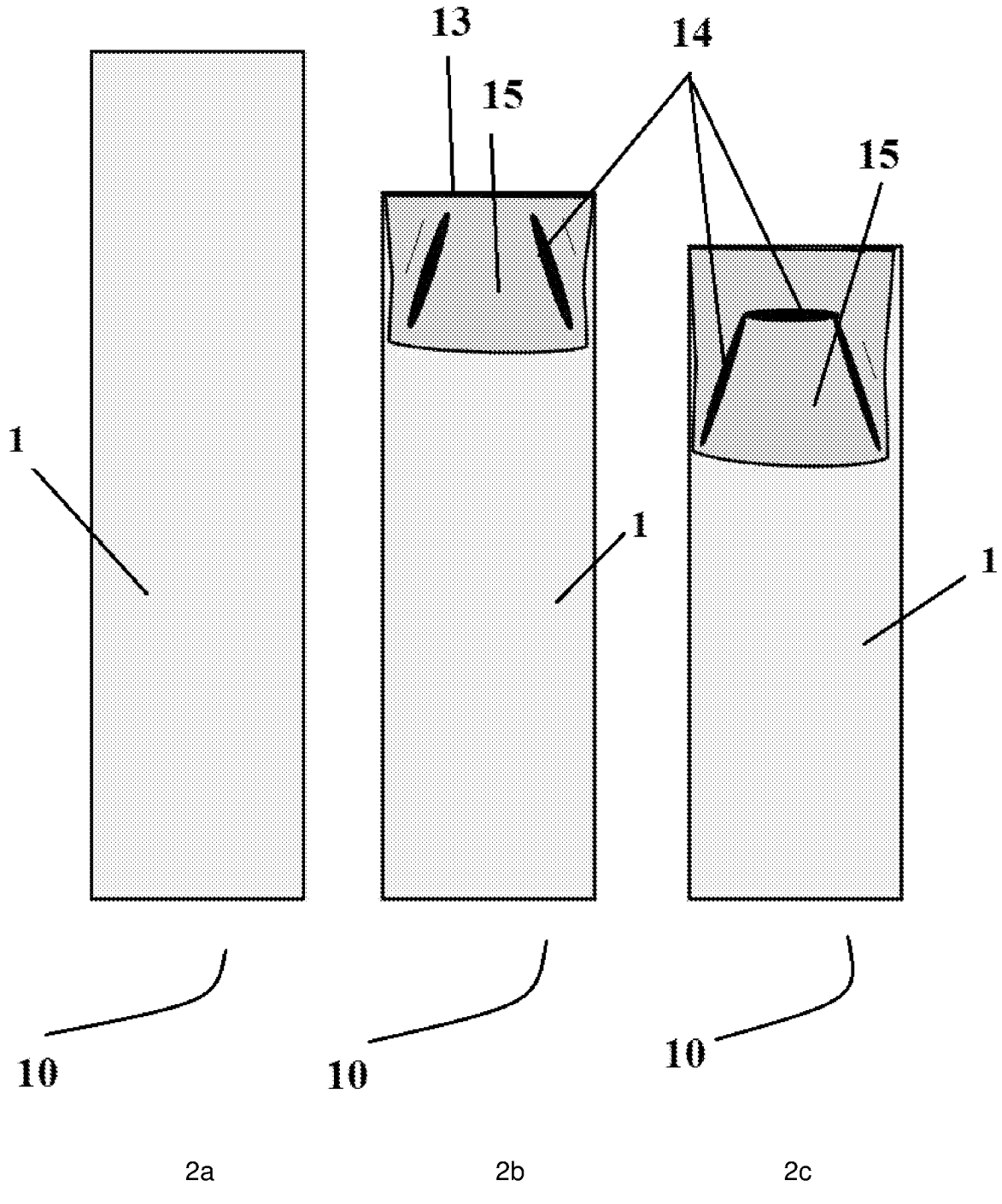
FIG. 2 represents a front view of other preferred embodiments of the invention wherein the sampling cloth is in the form of a single-sheet fabric having a folded area.

FIG. 2 depicts further embodiments of the sampling cloth (10) of the invention made from a single sheet (1) of fabric. FIG. 2a represents a front view of a rectangular sampling cloth (10) from which the preferred embodiments depicted in FIGS. 2b and 2c may be obtained by folding once the proximal end of the sampling cloth (10) along a folding line (13) and welding the folded area to the rest of the sheet (1) along guiding lines (14), thus defining pocket areas (15) for the insertion of an applicator. Preferably, the folding line (13) is substantially parallel with the short sides of said rectangular sampling cloth (10). In the embodiment of FIG. 2b, the pocket area (15) is delimited by two guiding elements (14) and the folded line (13), while in the embodiment of FIG. 2c the pocket area (15) is delimited by three guiding elements (14). In a preferred embodiment, the sampling cloth (10) in FIG. 2 has a length of more than 14 cm, preferably more than 16 cm, more preferably more than 18 cm; and a width of less than 6 cm, preferably less than 5 cm. In a preferred example, the folding line (13) is at a distance of about 2 cm to about 4 cm from the proximal end of the sampling cloth (10), thus obtaining a pocket (15) with dimensions sufficient to maintain the applicator (20) in place during insertion while at the same time maximizing the surface of the sample cloth (10) that remains in the form of one single sheet. The guiding elements (14) are placed so that the maximum distance between them is about 2-6 mm bigger than the diameter of the applicator (20), for a smooth insertion and removal of the applicator (20). In a preferred embodiment, for a sampling cloth (10) for vaginal use, the sampling cloth as depicted in FIG. 2 has, along the folding line (13), an area consisting of a rough material (not represented in the figure). Placing the rough material along the folding line (13) has the advantage that the rough material will have better chances of coming into contact with and sampling cells from the cervix.

The embodiments of FIGS. 2b and 2c are also depicted in FIGS. 3a and 3b, respectively, this time together with applicators. FIGS. 3a and 3b show how the sampling cloths (10) of the two embodiments are positioned on the applicators (20) before insertion into the bodily cavity. FIG. 3b further depicts another embodiment, wherein the sampling cloth (10) is provided with means for removal (16), for removing the sampling cloth (10) from the bodily cavity and also for sampling specimens from outside the bodily cavity. The means for removal (16) may consist of at least one thread or stripe.

As shown in FIG. 3b, the placing of the guiding elements (14) such that the proximal limit of the pocket (15) consists of a guiding line (14) placed underneath the folding line (13) has the advantage that a loop (18) of fabric is formed by the material of the sampling cloth (10) above the pocket (15). This loop (18) has the advantage that it better protects the bodily cavity from the impact of the applicator (20) at the moment of insertion and that it is also able to more thoroughly sample the specimens of the cervix. As mentioned before, a rougher material may be placed in the area of this loop (18) in order to efficiently sample specimens from the cervical area.

Figure 4:
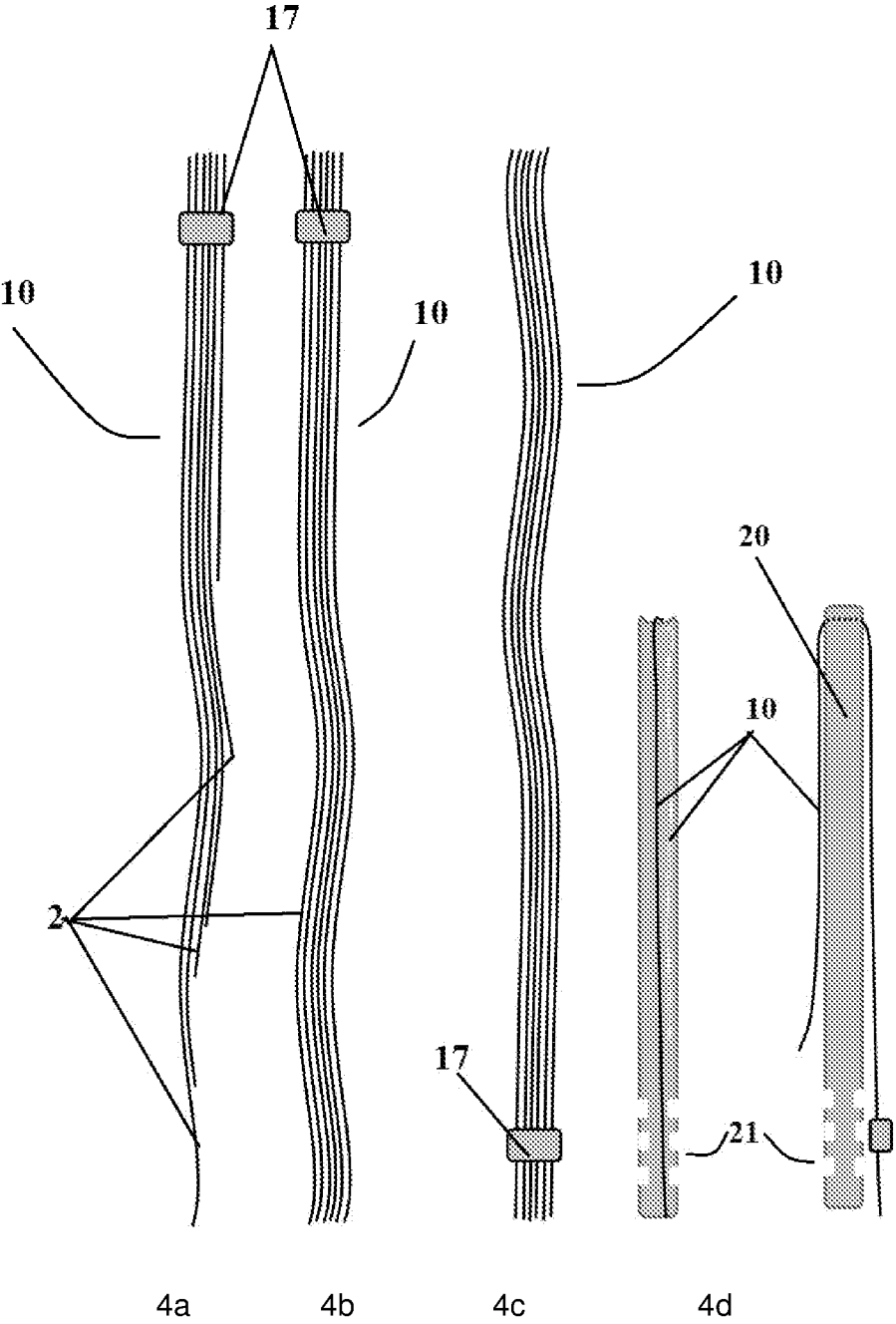
FIG. 4 represents a front view of different embodiments according to the invention wherein the sampling cloth is in the form of a multitude of fringes.

FIG. 4 depicts several embodiments according to the invention wherein the sampling cloth (10) is in the form of a multitude of fringes (2) of various lengths or of the same length, held together by a joining element (17), as well as an applicator (20) adapted for inserting such sample cloths (10) within a bodily cavity.

In the embodiment according to FIG. 4a, the fringes (2) have gradually increasing lengths, with one of the fringes (2) being long enough to protrude outside the bodily cavity and to be used as means of removal (16). In a preferred embodiment, the fringes (2) have lengths increasing gradually from about 4 cm to about 22 cm. Said fringes (2) are provided with means to hold them together in the form of joining elements (17).

FIG. 4d shows an applicator (20) having a proximal end provided with a depression for housing the fringes (2) of the sampling cloth during insertion.

Figure 5:
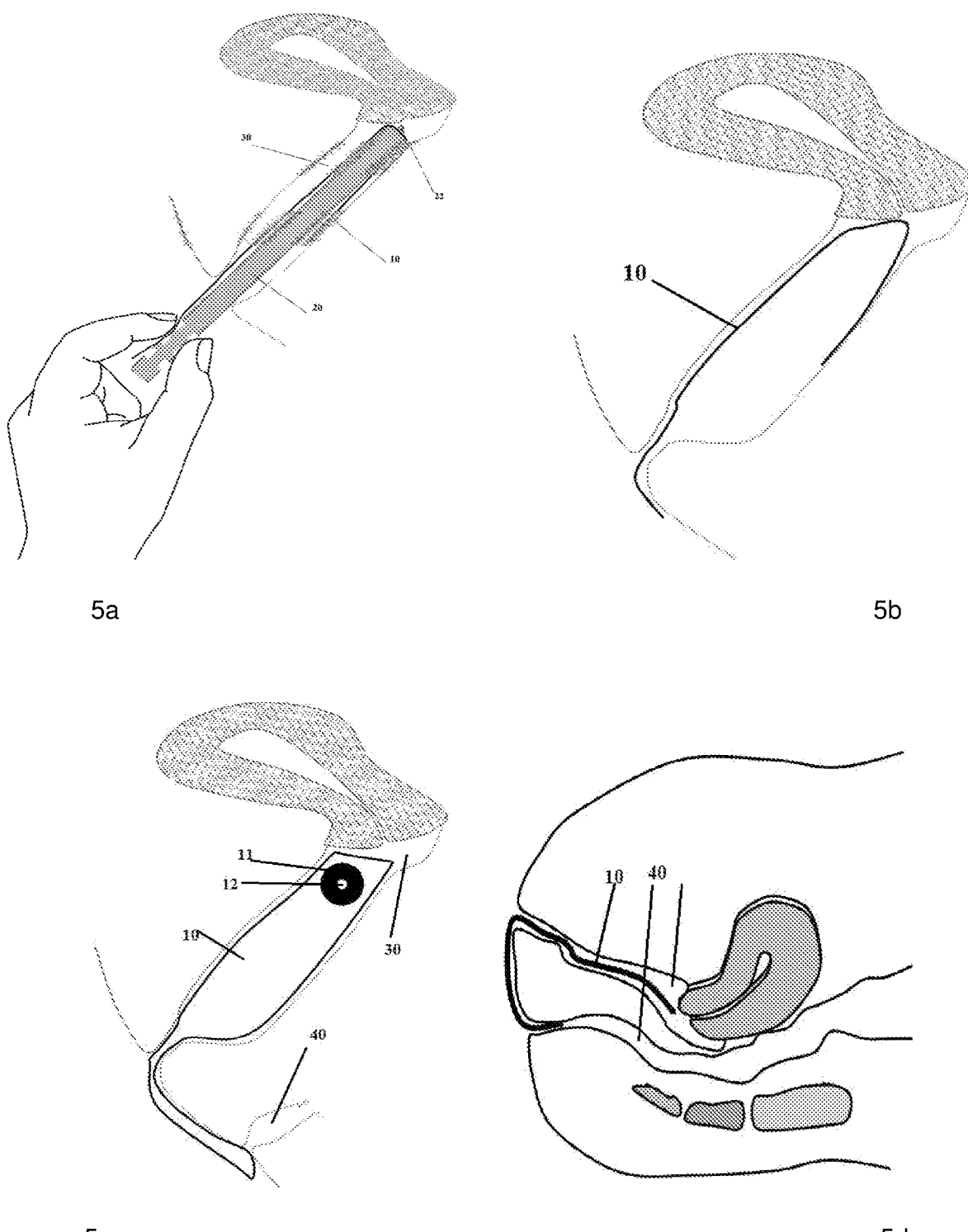
FIG. 5 represents sectional views of some preferred embodiments according to the invention, with a sampling cloth being inserted into a bodily cavity with an applicator, and various positions of the sampling cloth after removal of the applicator.

FIG. 5 represents sectional views of various embodiments according to the invention, showing the positioning of a sampling cloth (10) into the bodily cavity(es). FIG. 5a shows a sampling cloth (10) as depicted in FIG. 1 at the moment of insertion inside the vaginal cavity (30). It can be seen that the protuberance (22) of the applicator (20) protrudes from the orifice (12) of the pushing area (11) of the sampling cloth (10). Part of the sampling cloth (10) protrudes outside the vaginal cavity (30) and can be held in place together with the applicator (20) at the gripping area (21) of the applicator. FIG. 5b shows the position taken by the sampling cloth within the vaginal cavity (30) after removing the applicator (20). FIG. 5c depicts the sampling cloth (10) having a length sufficient to reach the anal orifice, while FIG. 5d shows the sampling cloth (10) inserted into the vaginal cavity (30) and having a length sufficient to be also inserted into the rectal cavity (40).

FIG. 6 represents views of the steps according to an embodiment of the invention for placing the sampling cloth (10) within a syringe-shaped recipient (50), closing and securing said recipient (50).

In a preferred embodiment depicted in FIG. 6, after removing the sample cloth (10) from the bodily cavity, it is placed in a recipient (50) having the shape of a syringe. Said recipient (50) comprises a barrel (51), a piston (52) and a discharge orifice (53) provided with sealing means (54). Also, the recipient (50) is further provided with stopping elements (55). FIG. 6a depicts the introducing of the sampling cloth (10) into the barrel (51) of the recipient (50). In FIG. 6b it is shown how the piston (52) of the syringe-like recipient (50) is inserted into the barrel (51). FIG. 6c illustrates a preferred embodiment wherein the recipient (50) is further provided with stopping elements for sealing the piston (52) in a closed position inside the barrel (51). In FIG. 6c, said stopping elements consist of an adjustable plastic strip (55) adapted to pass through an orifice (56) provided in the barrel (51) as well as through an orifice (57) provided in the piston (52), for example at its end. After the piston (52) is inserted into the barrel (51), the adjustable plastic strip (55) is passed through the orifices (56) and (57) and is closed in position (the length of its loop is adjusted to the desired length), thus sealing together the piston (52) and barrel (51) in the desired position. The use of such an adjustable strip (55) ensures that the piston (52) cannot exit the barrel (51) by accident, and it will function as an alarm signal (evidence) in case the recipient is tampered with.

FIG. 7 represents a comparative table, showing a representative comparison between results obtained for detecting HPV strains by using the sampling cloth (10) and self-sampling method according to the invention compared with the results obtained by using traditional (physician-collected) samples.

A lot of 91 women were using both the self-sampling method of the invention, and the traditional (physician-collected) sampling. The self-sampling method of the invention was performed using a sampling cloth (10) similar to the one depicted in FIG. 2b. Said sampling cloth (10) was made of a non-woven textile with a soft carded smooth surface comprising polyethylene and polyester, having an absorbency of 1.6 g/g as measured using Syngina protocol; a thickness of 0.25 mm, and dimensions of about 170×45 mm before being folded. The recipient (50) of the self-sampling kit was a plastic jar with a threaded cap. The women were advised to maintain the sampling cloth inside the vagina for about 3 hours.

The first line of the table in FIG. 7 shows all the known strains of HPV. The high-risk strains known to be responsible for causing cancer are marked with a letter c.

The second line of the table in FIG. 7 shows (marked with the letter x) the strains of HPV against which Vaccine G4 is effective.

The third line of the table in FIG. 7 shows (marked with the letter x) the strains of HPV against which Vaccine G9 is effective.

The following six lines of the table in FIG. 7 show the results obtained by testing women using the traditional method (of sampling by a gynecologist using a vaginal scraper with a swab). Marked with the sign+are the strains of HPV thus detected.

The next three lines of the table in FIG. 7 show the results obtained by testing the same women using the self-sampling kit and method of the invention as detailed above. Marked with the sign+are the strains of HPV detected by using self-sampling kit and method which have also been detected by the traditional method. It is evident that all the HPV strains detected by the traditional method where also detected in the samples obtained by using the kit and method of the invention. Moreover, by using the self-sampling kit and method according to the invention have been detected (marked with the sign ++) strains of HPV which have not been detected by the traditional method, including, for patient #006, the very dangerous HPV strain 16.

The total findings for all 91 patients have been compiled in the comparative Table 1 below.

The data in the table show that in ail cases the use of the method and kit of the invention resulted in a better detection than by using the traditional method (or at least similar detection). Especially for the detection of HPV strains the method and kit of the invention has yielded significantly better results. For example, the number of patients for which high-risk HPV strains have been detected by using the method and kit of the invention is almost double than the number of patients for which such strains have been detected using the traditional method (27 patients vs. 14 patients). Also, the figures show that by using the self-sampling method and kit of the invention, cervical cells (cellular DNA) is detected in every case (91 patients out of 91). Thus, surprisingly, the self-sampling method and kit of the invention is one hundred percent successful in sampling cervical cells of a quality necessary for diagnosis of cervical cancer, and the same sample can be also used for a very effective detection of HPV and other specimens.

While the present invention has been described with reference to exemplary embodiments, it is to be understood that the invention is not limited to the disclosed exemplary embodiments. The scope of the claims is to be accorded the broadest interpretation so as to encompass all such modifications and equivalent structures and functions.

The invention claimed is:

1. A method of using a sampling cloth (10), comprising self-sampling at least one specimen from bodily cavity side walls of humans or animals for diagnosis, wherein said sampling cloth (10) consists of a single sheet of flexible fabric with a total absorbency of less than 2.8 g and a thickness of 2 mm or less.

2. A method for self-sampling at least one specimen from bodily cavities of humans or animals for diagnosis, the method comprising the steps:

TABLE 1

| Specimens to be detected | Results obtained using the sampling made by a trained specialist using a cervical scraper (swab) | Results obtained using the self-sampling method and kit of the invention |
| --- | --- | --- |
| Total number of patients tested | 91 | 91 |
| HPV - number of patients with both low-risk and high risk strains of HPV detected | 20 | 33 |
| HPV - Average number of HPV detected - both low-risk and high risk strains - | 0.50/sample | 0.80/sample |
| HPV - number of patients with high-risk strains of HPV detected | 14 | 27 |
| HPV - Average number of HPV strains detected - high risk strains only - | 0.35/sample | 0.51/sample |
| Number of patients for which Ubiquitous cellular genes - cellular DNA was detected | 91 | 91 |
| number of patients detected with Chlamidia trachomatis | 1 | 1 |
| number of patients detected with Neisseria gonorrheae | 1 | 1 |
| number of patients detected with Mycoplasma genitalium | 3 | 3 |
| number of patients detected with Mycoplasma hominis | 7 | 9 |
| number of patients detected with Ureaplasma urealyticum | 9 | 11 |
| number of patients detected with Ureaplasma parvum | 40 | 41 |
| number of patients detected with Trichomonas vaginalis | 1 | 1 |
| number of patients detected with Vaginal bacteria | 62 | 67 | a) inserting a sampling cloth (10) consisting of a single sheet of flexible fabric with a total absorbency of less than 2.8 g and thickness of 2 mm or less into a bodily cavity of a human or animal to collect specimen material from a side wall of the bodily cavity;

b) removing the sampling cloth (10) from the bodily cavity; and c) taking or sending the sampling cloth (10) to a testing facility for diagnosis.

3. The method for self-sampling according to claim 2, further comprising the steps:

a) placing the sampling cloth (10) inside a sealable recipient; and b) sealing the sealable recipient after placing the sampling cloth (10) inside the sealable recipient and before taking or sending the sampling cloth (10) to the testing facility.

4. The method for self-sampling according to claim 3, wherein the sampling cloth (10) is left inserted into the bodily cavity for a period of time of at least 30 minutes.

5. A method for diagnostic of STIs (Sexually Transmitted Diseases) comprising the steps of:

a) self-sampling at least one specimen from bodily cavities of humans and animals according to the method of claim 2, and b) determining a presence of a STI by analyzing and identifying said at least one specimen from the sampling cloth (10).

6. The method of claim 5, wherein said sampling cloth (10) has dimensions so that, after insertion, part of said sampling cloth (10) protrudes outside the bodily cavity.

7. The method of claim 5, wherein said sampling cloth (10) is made of at least one sheet of fabric (1) and/or comprises one or more fringes (2).

8. The method of claim 7, wherein at least one of the fringes (12) has a length sufficient to protrude outside the bodily cavity.

9. The method of claim 5, wherein said sampling cloth (10) is further provided with at least one thread, string, strip, ribbon, or wire for removing said sampling cloth (10) from the bodily cavity.

10. The method of claim 5, wherein the sampling cloth (10) has a region having a rougher surface than an area of the sampling cloth outside the region, the region having the rougher surface being situated to collect specimen material.

11. The method of claim 10, wherein the region having the rougher surface is integrally formed with the area of the sampling cloth outside the region.

12. The method of claim 10, wherein the region having the rougher surface is attached to the area of the sampling cloth outside the region by gluing, welding or sewing.

13. The method of claim 10, wherein the sampling cloth (10) is made of a non-woven textile made of synthetic fibers.

14. The method of claim 13, wherein the non-woven textile is thermo-fusible.

15. The method of claim 14, wherein the non-woven textile comprises a polyethylene-polyester bicomponent.

16. The method for self-sampling according to claim 2, wherein the flexible fabric has an absorbency of less than 2 g/g.

17. The method for self-sampling according to claim 2, wherein the single sheet of flexible fabric is in a rectangular shape having a width of from 2 cm to 6 cm, a length of from 3.5 cm to 22 cm, and an absorbency of less than 3 g/g.

* * * * *